(12) United States Patent
Just et al.

(10) Patent No.: US 11,246,535 B2
(45) Date of Patent: *Feb. 15, 2022

(54) ELECTRODE SUPPORT STRUCTURE ASSEMBLIES

(71) Applicant: ST JUDE MEDICAL, ATRIAL FIBRILLATION DIVISION, INC, St. Paul, MN (US)

(72) Inventors: Dale E. Just, Minneapolis, MN (US); Troy T. Tegg, Elk River, MN (US); Theodore A. Johnson, St. Paul, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 339 days.

This patent is subject to a terminal disclaimer.

(21) Appl. No.: 16/216,738

(22) Filed: Dec. 11, 2018

(65) Prior Publication Data

US 2019/0239811 A1   Aug. 8, 2019

Related U.S. Application Data

(63) Continuation of application No. 14/340,156, filed on Jul. 24, 2014, now Pat. No. 10,182,762, which is a
(Continued)

(51) Int. Cl.
*A61B 5/042* (2006.01)
*A61B 18/14* (2006.01)
(Continued)

(52) U.S. Cl.
CPC ............ *A61B 5/6859* (2013.01); *A61B 5/287* (2021.01); *A61B 5/6858* (2013.01);
(Continued)

(58) Field of Classification Search
CPC ...... A61B 18/1492; A61B 2018/00214; A61B 2018/00839; A61B 5/287;
(Continued)

(56) References Cited

U.S. PATENT DOCUMENTS 4,699,147 A    10/1987  Chilson et al.
5,345,936 A *  9/1994   Pomeranz .............. A61N 1/056
                                                          600/374
(Continued)

*Primary Examiner* — Joseph A Stoklosa
*Assistant Examiner* — Brian M Antiskay
(74) *Attorney, Agent, or Firm* — Dykema Gossett PLLC

(57) ABSTRACT

An electrode support structure assembly is provided comprising an electrode support structure including a plurality of splines. Each of the plurality of splines can have a proximal end portion and a distal end portion. The assembly further comprises a first element defining an axis and comprising an outer surface. The outer surface comprises a plurality of slots configured to receive the distal end portion of each of the plurality of splines. The first element is configured such that the distal end portion of each of the plurality of splines may move with respect to each slot. In accordance with some embodiments, the distal end portion of each of the plurality of splines comprises a section configured for engagement with the first element, wherein the section comprises a shoulder.

20 Claims, 13 Drawing Sheets

Related U.S. Application Data continuation of application No. 13/340,760, filed on Dec. 30, 2011, now Pat. No. 8,825,130.

(51) Int. Cl.
    *A61B 5/00*        (2006.01)
    *A61B 5/287*      (2021.01)
    *A61B 18/00*      (2006.01)

(52) U.S. Cl.
    CPC .............. *A61B 18/1492* (2013.01); *A61B 2018/00267* (2013.01); *A61B 2018/1475* (2013.01); *A61B 2218/002* (2013.01)

(58) Field of Classification Search
    CPC ........ A61B 2018/00267; A61B 5/6858; A61B 2018/00351; A61B 2017/00243; A61B 2018/1467; A61B 2017/00867; A61B 2017/00053; A61B 5/06; A61B 5/6853; A61N 1/056; A61N 1/05
    USPC ............ 600/372–374, 377, 381, 434–435, 600/508–509; 604/164.03, 508–509; 607/115–116, 122–124, 131
    See application file for complete search history.

(56) References Cited

U.S. PATENT DOCUMENTS

| | | |
|---|---|---|
| 5,549,108 A | 8/1996 | Edwards et al. |
| 5,551,426 A * | 9/1996 | Hummel ............... A61B 5/287 600/374 |
| 5,647,870 A | 7/1997 | Kordis et al. |
| 5,772,590 A | 6/1998 | Webster, Jr. |
| 5,782,239 A | 7/1998 | Webster, Jr. |
| 5,855,552 A | 1/1999 | Houser et al. |
| 5,871,483 A | 2/1999 | Jackson et al. |
| 5,893,847 A | 4/1999 | Kordis |
| 5,911,739 A | 6/1999 | Kordis et al. |
| 5,925,038 A | 7/1999 | Panescu et al. |
| 5,928,228 A | 7/1999 | Kordis et al. |
| 5,964,753 A | 10/1999 | Edwards |
| 6,119,030 A | 9/2000 | Morency |
| 6,163,716 A | 12/2000 | Edwards et al. |
| 6,216,043 B1 | 4/2001 | Swanson et al. |
| 6,669,693 B2 * | 12/2003 | Friedman ............ A61B 18/1492 606/41 |
| 6,741,878 B2 | 5/2004 | Fuimaono et al. |
| 6,748,255 B2 | 6/2004 | Fuimaono et al. |
| 6,973,340 B2 | 12/2005 | Fuimaono et al. |
| 7,149,563 B2 | 12/2006 | Fuimaono et al. |
| 7,257,434 B2 | 8/2007 | Fuimaono et al. |
| 7,742,795 B2 | 6/2010 | Stone et al. |
| 7,955,299 B2 | 6/2011 | Just et al. |
| 8,364,234 B2 | 1/2013 | Kordis et al. |
| 8,825,130 B2 | 9/2014 | Just et al. |
| 9,993,160 B2 * | 6/2018 | Salvestro ................ A61B 5/01 |
| 2003/0114739 A1 | 6/2003 | Fuimaono et al. |
| 2004/0133091 A1 | 7/2004 | Fuimaono et al. |
| 2006/0009690 A1 | 1/2006 | Fuimaono et al. |
| 2007/0276212 A1 | 11/2007 | Fuimaono et al. |
| 2011/0213231 A1 | 9/2011 | Hall et al. |
| 2015/0080693 A1 | 3/2015 | Solis |

\* cited by examiner

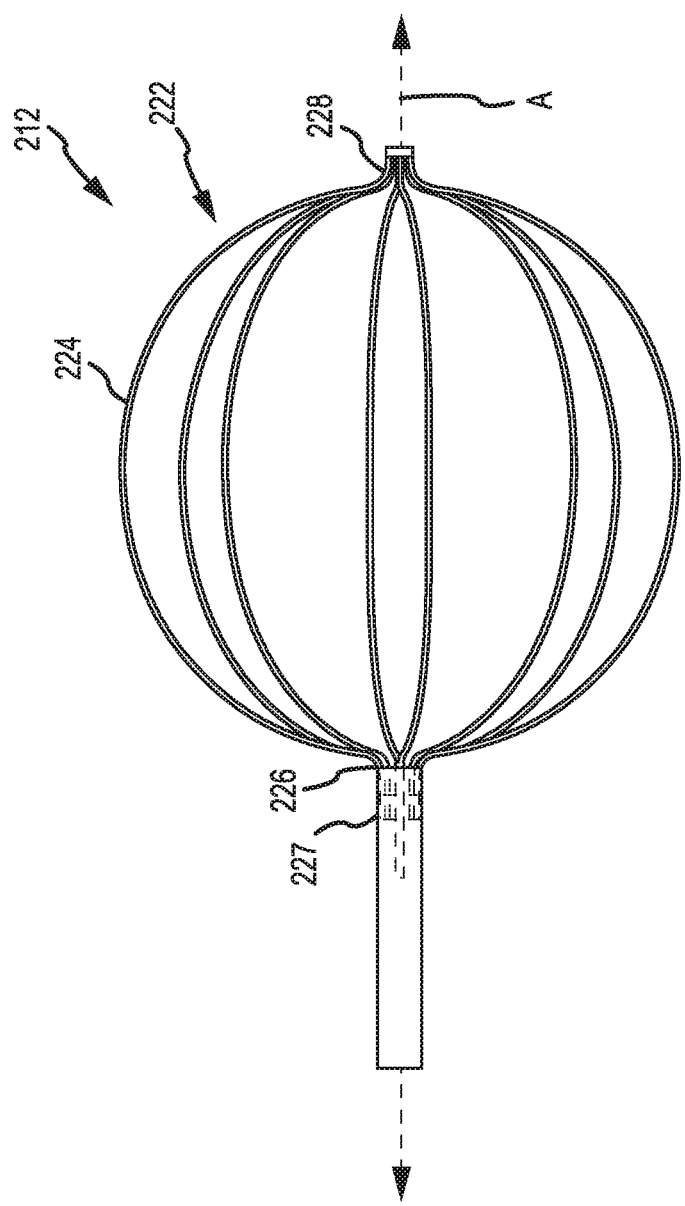

ELECTRODE SUPPORT STRUCTURE ASSEMBLIES

CROSS REFERENCE TO RELATED APPLICATIONS

This application is a continuation of U.S. application Ser. No. 14/340,156, filed 24 Jul. 2014 (the '156 application), which is a continuation of U.S. application Ser. No. 13/340,760, filed 30 Dec. 2011 (the '760 application), now U.S. Pat. No. 8,825,130. The '156 application and the '760 application are both hereby incorporated by reference in their entirety as though fully set forth herein.

BACKGROUND OF THE INVENTION a. Field of the Invention

The instant disclosure relates generally to electrode support structure assemblies. In particular, the instant disclosure relates to electrode support structure assemblies for basket catheters including a plurality of splines.

b. Background Art

Electrophysiology catheters are used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

Typically, a catheter is deployed and manipulated through a patient's vasculature to the intended site, for example, a site within a patient's heart or a chamber or vein thereof. The catheter carries one or more electrodes that can be used for cardiac mapping or diagnosis, ablation and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents errant conduction signals that can form the basis for arrhythmias.

Various catheters and electrode arrangements can be employed for different purposes. Catheters having basket-shaped electrode support structures are known and described in, for example and without limitation, U.S. Pat. No. 5,772,590 entitled "Cardiovascular Catheter with Laterally Stable Basket-Shaped Electrode Array with Puller Wire," the entire disclosure of which is incorporated herein by reference as though set forth in its entirety. Generally, catheters having basket-shaped electrode support structures are introduced through a guiding sheath with the electrode support structure in a folded or collapsed position within the sheath so that the electrode support structure does not damage tissue during its introduction. Once the catheter reaches its intended position within the heart, the guiding sheath can be removed and the electrode support structure can be allowed to radially outwardly expand for cardiac mapping or diagnosis, ablation and/or other therapy delivery modes, or both, for example.

Typically, basket-shaped electrode support structures comprise a plurality of splines that can be formed from laser cut tubing and be integral at one end or that comprise discrete, separate elements. The distal ends of each of these plurality of splines generally must be joined together. For example, the distal ends of each of the plurality of splines can be mounted around a first piece of tubing and then be held in place by a second piece of tubing as generally described and illustrated in U.S. Patent Application Publication No. 2007/0276212 entitled "Basket Catheter With Improved Expansion Mechanism," the entire disclosure of which is hereby incorporated by reference as though set forth in its entirety.

It is desirable for each of the splines to be joined in such a way that the splines are configured to straighten evenly when the electrode support structure is collapsed. However, it may be difficult for the electrode support structure to collapse evenly if manufacturing variances have resulted in differences in the individual lengths of the splines. It may also be difficult for the electrode support structure to collapse evenly if one or more of the splines have experienced a change in length relative to the remainder of the splines, such as during manipulation of the electrode support structure around a curve, for example. If the splines do not straighten evenly when the electrode support structure is collapsed, a protrusion or "loop" can form at the distal end of one or more of the plurality of splines. Continued collapse or multiple collapses of the electrode support structure can potentially cause fatigue at the point of the protrusion or "loop" and ultimately fracture the spline. Moreover, when the distal ends of the splines are fixed in place (e.g., mounted between two pieces of tubing), the distal flexibility of the splines may be limited, thereby adversely impacting the collapsibility of the electrode support structure. In addition, stress imparted at the distal end of the electrode support structure during collapse and/or expansion of the electrode support structure can also result in the failure of any strut or other element that may be configured to join the distal ends of the splines together.

Additionally, when the electrode support structure is in an expanded state, electrode distribution may not be uniform in accordance with some electrode arrangements. Moreover, during collapse of the electrode support structure (e.g., when the electrode support structure is emerging from or being retracted into a delivery sheath), some electrode arrangements may possibly result in electrode to electrode contact and/or short circuits, which may cause electrode wear and/or limit electrode functionality. In addition, some electrode arrangements may not minimize the profile of the electrode support structure during collapse of the electrode support structure, which can result in electrode damage when the electrode support structure is being delivered through the delivery sheath, especially when being delivered through a tortuously angulated pathway.

Typically, basket-shaped electrode support structures can include an expander having a distal end attached to a distal end of the electrode support structure. The expander includes a proximal end that extends out of a proximal end of a catheter or other medical device employing the electrode support structure to a control handle. The expander can be moved longitudinally relative to the catheter or other medical device to expand and contract the electrode support structure. The expander is generally coaxial with the catheter. An expander will not generally allow for free axial movement of the electrode support structure if the electrode support structure is being diametrically constrained in some way.

There is therefore a need to minimize and/or eliminate one or more of the problems as set forth above. The foregoing discussion is intended only to illustrate the present field and should not be taken as a disavowal of claim scope.

BRIEF SUMMARY OF THE INVENTION

It is desirable to provide an electrode support structure assembly that can include an element joining the distal end of each of the plurality of splines that is configured to provide freedom for each of the plurality of splines to move independently along an axis of the electrode support structure. This may help ensure that the splines are configured to straighten evenly when the electrode support structure is collapsed. It is also desirable to provide an electrode support structure assembly that can include an element joining the distal end of each of the plurality of splines that is configured to provide freedom for each of the plurality of splines to articulate relative to an axis of the electrode support structure such that each of the plurality of splines can be positioned at numerous angles relative to the axis of the electrode support structure in order to minimize stress imparted at the distal end of the electrode support structure during collapse and/or expansion. It is also desirable to provide an improved electrode arrangement that may provide more uniform electrode distribution when the electrode support structure is in its deployed or expanded state, while at the same time providing a smaller profile when in a collapsed state so as prevent electrode to electrode short circuits. It is also desirable to provide an electrode support structure that can be configured to allow for free, uniform axial displacement even if the electrode support structure is being diametrically constrained in some way.

An electrode support structure assembly is provided comprising an electrode support structure comprising a plurality of splines and a first element. Each of the plurality of splines can have a proximal end portion and a distal end portion opposing the proximal end portion. The first element can define an axis and comprise an outer surface. The outer surface can comprise a plurality of slots configured to receive the distal end portion of each of the plurality of splines. The first element is configured such that the distal end portion of each of the plurality of splines may move with respect to each slot. In accordance with some embodiments, the distal end portion of each of the plurality of splines comprises a section configured for engagement with the first element, wherein the section comprises a shoulder. In other words, a distal end of the distal end portion of each of the plurality of splines can have an increased diameter relative to the remainder of the distal end portion of each of the plurality of splines.

In accordance with a first embodiment of the disclosure, the first element comprises a generally cylindrical member and the plurality of slots comprise grooves on the outer surface. The grooves can extend along the axis of the first element and can be configured to allow each of the plurality of splines to move along the axis of the first element a select distance. Still in accordance with a first embodiment of the disclosure, the electrode support structure assembly can further comprise a second element configured for engagement with the first element to retain the distal end portion of each of the plurality of splines within the plurality of slots of the first element. The second element can comprise a cap having at least a portion thereof configured to be disposed radially outwardly of the first element. The cap can further comprise an axial end. The axial end can be separated from the first element by a select distance to allow for movement of each of the plurality of splines along the axis of the first element. In accordance with some embodiments of the disclosure, the electrode support structure assembly can further include a third element comprising a generally cylindrical member having an outer radial surface including a plurality of channels configured to receive the proximal end portion of each of the plurality of splines. The proximal end portion of each of the plurality of splines can comprise a section configured for engagement with the third element, wherein the section comprises a shoulder. A proximal end of the proximal end portion of each of the plurality of splines can have an increased diameter relative to the remainder of the proximal end portion of each of the plurality of splines in accordance with some embodiments of the disclosure.

In accordance with a second embodiment of the disclosure, the first element can comprise a cap having an axial end and a radially extending wall. Each of the plurality of slots can extend through the radially extending wall. Each of the plurality of slots can extend along the axis of the first element. Each of the plurality of slots can be configured to allow each of the plurality of splines to articulate from a first position in which the distal end portion of the spline is disposed at a first angle relative to the axis of the first element to a second position in which the distal end portion of the spline is disposed at a second angle relative to the axis of the first element, wherein the first angle is different than the second angle. The cap further comprises an axial end separated from the second element by a select distance to allow for movement of each of the plurality of splines. Still in accordance with a second embodiment of the disclosure, the electrode support structure assembly can further comprise a second element configured for engagement with the first element to retain the distal end portion of each of the plurality of splines within the plurality of slots of the first element. The second element can comprise a generally cylindrical member with an outer radial surface having at least a portion thereof configured to be disposed radially inwardly of the first element. In particular, the second element can comprise a fluid coupler having a first end configured to mate with the first element and a second end configured to mate with a tubing assembly.

In accordance with some embodiments of the disclosure, the plurality of splines includes a first spline and a second spline. The first spline can include a first plurality of electrodes spaced apart on the first spline, and the second spline can include a second plurality of electrodes spaced apart on the second spline. In accordance with some embodiments of the disclosure, the first plurality of electrodes can be substantially evenly spaced apart on the first spline, and the second plurality of electrodes can be substantially evenly spaced apart on the second spline. Each of the second plurality of electrodes on the second spline can be in a staggered position relative to the position of each of the first plurality of electrodes on the first spline. For example and without limitation, at least one of the second plurality of electrodes on the second spline can be located on the second spline at a position that is in substantially the same plane as the midpoint between two of the first plurality of electrodes on the first spline. A first distance between a distal-most electrode of the first plurality of electrodes and a distal end of the first spline can be substantially the same as a second distance between a proximal-most electrode of the second plurality of electrodes and a proximal end of the second spline in accordance with some embodiments of the disclosure.

An electrode support structure assembly in accordance with a third embodiment of the disclosure is also provided. The assembly includes an electrode support structure comprising a proximal end and a distal end and defining longitudinal axis. The electrode support structure is configured to be radially outwardly expandable relative to the longitudinal axis to an expanded arrangement and radially inwardly collapsible relative to the longitudinal axis to a collapsed arrangement. The electrode support structure can further include a plurality of splines. Each of the plurality of splines can have a proximal end portion and a distal end portion opposing the proximal end portion. The distal end portion of each of the plurality of splines can comprise a first connection element configured to connect the distal end portion to a first adjacent spline; and a second connection element configured to connect the distal end portion to a second adjacent spline, wherein the first connection element, second connection element, and each of the plurality of splines are integrally formed. In addition, at least a portion of the distal end portion of each of the plurality of splines can be disposed substantially along the longitudinal axis of the electrode support structure. The electrode support structure assembly can further comprise a sheath. Movement of the proximal end of the electrode support structure relative to the sheath can be configured to expand and collapse the electrode support structure.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIGS. 12A-12C are lateral elevational views of an electrode support structure in accordance with a fourth embodiment of the disclosure illustrating the deployment of the electrode support structure.

DETAILED DESCRIPTION OF THE DISCLOSURE

Figure 1:
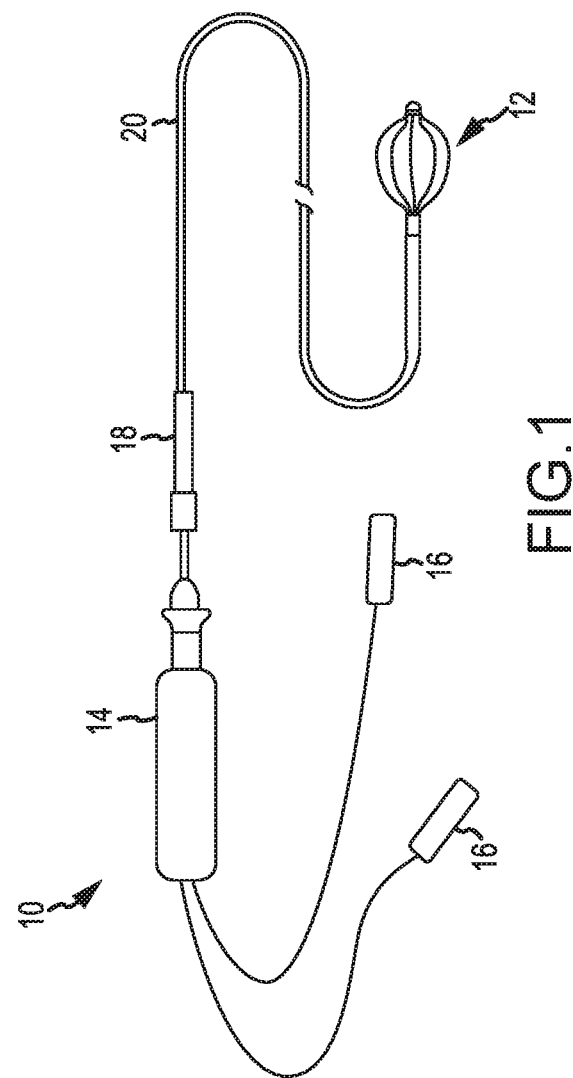
FIG. 1 is a side view of a catheter system employing an electrode support structure assembly in accordance with a first embodiment of the disclosure.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

The instant disclosure generally relates to electrode support structures. For purposes of this description, similar aspects among the various embodiments described herein will be referred to by similar reference numbers. As will be appreciated, however, the structure of the various aspects can be different among the various embodiments.

Referring now to FIG. 1, a side view of an intracardiac catheter system 10 employing an electrode support structure assembly 12 in accordance with a first embodiment of the disclosure is generally illustrated. The catheter system 10 includes a handle 14 and connectors 16 disposed proximal to the handle 14 for making electrical connections to a visualization, navigation, and/or mapping system (not shown) such as those systems available under the name ENSITE NAVX™ (aka ENSITE™ Classic as well as newer versions of the ENSITE™ system, denoted as ENSITE VELOCITY™) and available from St. Jude Medical, Inc. The handle 14 can have a uni-directional design, a bi-directional design, or any other suitable design and be accordingly configured to steer the electrode support structure assembly 12. The catheter system 10 can also include an introducer 18 located distally of the handle 14 that may be used to deliver an elongated catheter body 20 into the body of a patient, through a hemostasis valve of another, longer introducer, for example. The elongated catheter body 20 can extend from the introducer 18. The electrode support structure assembly 12 is configured to extend from the distal end of the elongated catheter body 20. The elongated catheter body 20 can comprise an elongated tubular construction having one or more lumens. The elongated catheter body 20 can be flexible or bendable. The elongated catheter body 20 can be of any suitable construction and made of any suitable material as known to those of ordinary skill in the art. The elongated catheter body 20 can have any outer diameter, but may generally be less than about 8 French. The elongated catheter body 20 can have an outer wall of any thickness, but may generally be configured so that one or more lumens can be disposed within the elongated catheter body 20 to accommodate pull wires, lead wires, sensor cables, and any other wires, cable, and/or tubes that may be needed in particular applications. The handle 14, connectors 16, introducer 18, and elongated catheter body 20 can be readily modified as dictated by the aesthetic or functional needs of particular applications. Although the electrode support structure assembly 12 is described and illustrated in connection with an intracardiac catheter system 10, the electrode support structure assembly 12 may be utilized in connection with other types of medical devices, such as for example and without limitation, stone retrieval baskets, distal protection devices, renal artery ablation devices, snares, and other retrieval devices.

Figure 2:
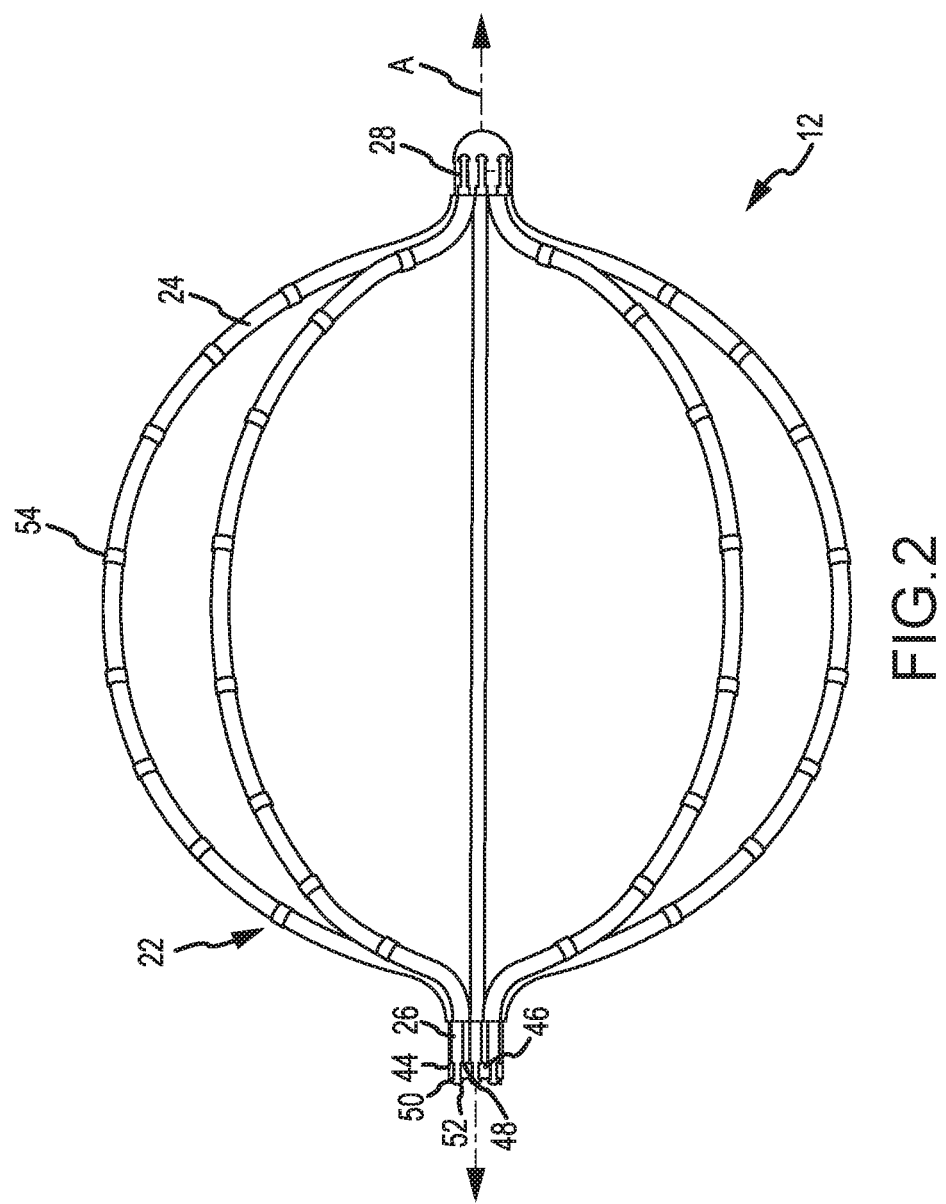
FIG. 2 is a lateral elevational view of an electrode support structure assembly in accordance with a first embodiment of the disclosure.

Referring now to FIG. 2, an elevational view of the electrode support structure assembly 12 in accordance with a first embodiment of the disclosure is generally illustrated. The electrode support structure assembly 12 is mounted to the distal end of the elongated catheter body 20. The electrode support structure assembly 12 comprises an electrode support structure 22. The electrode support structure 22 defines a longitudinal axis (A). The electrode support structure 22 comprises a plurality of splines 24. The splines 24 are deflectable elongated elements. The plurality of splines 24 can be configured to assume different configurations. For example and without limitation, the electrode support structure 22 can comprise a "basket" in which each of the plurality of splines 24 can splay or bow radially outwardly. The particular shape of the "basket" can vary. For example and without limitation, one or more of the plurality of splines 24 can splay or bow radially outwardly substantially uniformly along the length of the electrode support structure 22, away from longitudinal axis (A), or one or more of the plurality of splines 24 can splay or bow radially outwardly in varying amounts along the length of the electrode support structure 22. The resulting "basket" is generally symmetric about the longitudinal axis (A) of the electrode support structure 22 in accordance with some embodiments of the disclosure. As used herein, the term "basket" is not limited to the illustrated configuration, but can include other designs such as spherical or egg-shaped designs, for example. Although a "basket" shape is mentioned in detail, the plurality of splines 24 can assume any number of other shapes in accordance with various embodiments of the disclosure.

Each of the plurality of splines 24 can comprise a flexible wire with a non-conductive covering in accordance with some embodiments of the disclosure. The flexible wire can comprise a flat Nitinol wire in accordance with some embodiments of the disclosure. The non-conductive covering can comprise a biocompatible plastic tubing, such as polyurethane or polyimide tubing in accordance with some embodiments of the disclosure. Although these materials are mentioned in detail, the splines 24 can be made of any other suitable materials known to those of ordinary skill in the art. For example and without limitation, the splines 24 can be designed without internal flexible wires if a sufficiently rigid non-conductive material is used. The electrode support structure assembly 12 can further comprise one or more electrodes 54 supported by one or more of the plurality of splines 24. For example, one or more of the plurality of splines 24 can have one or more electrodes 54 mounted on the non-conductive covering in accordance with various embodiments of the disclosure. The number and spacing of the electrodes 54 on the plurality of splines 24 can vary in accordance with various embodiments of the disclosure.

Figure 3:
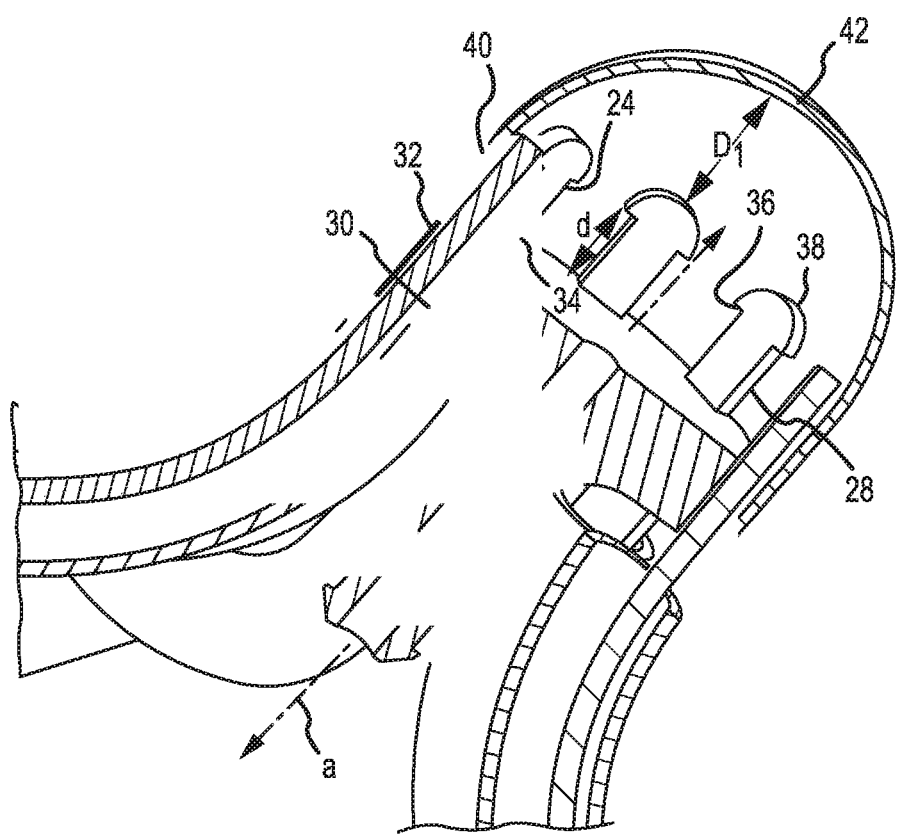
FIG. 3 is a close-up, perspective cross-sectional view of a portion of the electrode support structure assembly of FIG. 2.

Each of the plurality of splines 24 has a proximal end portion 26 and a distal end portion 28 opposing the proximal end portion 26 as best shown in FIGS. 2-3. For example and without limitation, the electrode support structure 22 may include eight splines 24. Although eight splines 24 are mentioned in detail, there may be fewer or more splines 24 in accordance with various embodiments of the disclosure. Each of the plurality of splines 24 may generally be evenly spaced circumferentially around the axis (A) of the electrode support structure 22.

The electrode support structure 22 is configured to be radially outwardly expandable relative to its axis (A) to an expanded arrangement as shown in FIGS. 1-3. The electrode support structure 22 is also configured to be radially inwardly collapsible relative to its axis (A) to a collapsed arrangement. The plurality of splines 24 of the electrode support structure 22 can be collapsed by an application of force. Upon removal of the application force, the plurality of splines 24 may return to the expanded arrangement. This expansion and collapse of the electrode support structure 22 may be achieved by using a shape memory material for the plurality of splines 24 in accordance with some embodiments of the disclosure. The expansion and collapse of the electrode support structure 22 may be achieved by using a biasing mechanism in accordance with other embodiments of the disclosure. For example and without limitation, an expander or tensor (not shown) may be coaxial with the elongated catheter body 20. The expander or tensor can have a distal end at the distal end portion 26 of the electrode support structure 22 and a proximal end extending out the proximal end of the elongated catheter body 20 and attached to the control handle 14. Longitudinal movement of the tensor relative to the elongated catheter body 20 can cause expansion and contraction of the electrode support structure 22. The tensor can comprise any material sufficiently rigid to achieve this function.

The electrode support structure assembly 12 further comprises a first element 30. Referring now to FIG. 3, the first element 30 is a generally cylindrical member having an axis (a). The first element 30 comprises an outer radial surface 32 located about the axis (a). The outer radial surface 32 includes a plurality of slots 34. The plurality of slots 34 are substantially evenly circumferentially spaced around the outer radial surface 32 of the first element 30. Each of the plurality of slots 34 is configured to receive the distal end portion 28 of each of the plurality of splines 24. In accordance with an embodiment of the disclosure, each of the plurality of slots 34 can comprise grooves 34 on the outer radial surface 32 in which the splines 24 can be slidingly disposed. The grooves 34 can extend along the axis (a) of the first element 30. The grooves 34 can be configured to allow each of the plurality of splines 24 to move (e.g., slide) along the axis (a) of the first element 30 a select distance (d). Accordingly, the first element 30 is configured to provide freedom for the splines 24 to move independently along the axis (a) of the first element 30. For example and without limitation, the first element 30 may be configured to allow each of the plurality of splines 24 to independently, axially travel a distance (d) from 0 to about 0.100 inches (about 2.54 mm). Although this particular range for distance (d) is mentioned in detail, the first element 30 may be configured to allow each of the plurality of splines 24 to independently, axially travel a distance (d) that is greater or smaller in accordance with other embodiments of the disclosure.

The distal end portion 28 of each of the plurality of splines 24 can comprise a section configured to restrain the axial slide movement of each of the plurality of splines 24 so as to keep each of the plurality of splines 24 within the first element 30 of the electrode support structure assembly 12. For example and without limitation, the section of the distal end portion 28 can comprise a shoulder 36. In other words, a distal end 38 of the distal end portion 28 of each of the plurality of splines 24 has an increased diameter relative to the remainder of the distal end portion 28 of each of the plurality of splines 24, thereby forming the shoulder 36 in each of the plurality of splines 24.

Referring now to FIGS. 2-3, the electrode support structure assembly 12 further comprises a second element 40. Second element 40 is configured for engagement with the first element 30 to retain the distal end portion 28 of each of the plurality of splines 24 within the plurality of slots 34 on the first element 30. In accordance with the first embodiment of the disclosure as generally illustrated in FIGS. 2-3, the second element 40 comprises a cap having at least a portion thereof that is configured to be disposed radially outwardly of the first element 30. Accordingly, the cap 40 can be configured to radially and/or axially confine each of the plurality of splines 24. The cap 40 further comprises an axial end 42 in accordance with some embodiments of the disclosure. The axial end 42 of the cap 40 is separated from the first element 30 by a select distance ($D_1$) to allow for movement of each of the plurality of splines 24 along the axis (a) of the first element 30. Although the second element 40 is described and illustrated as a cap, the second element 40 can comprise a ring in accordance with other embodiments of the disclosure. The ring can be configured to radially confine the plurality of splines 24 and also allow for movement of each of the plurality of splines 24 along the axis (a) of the first element 30.

Referring back to FIG. 2, in accordance with some embodiments of the disclosure, the electrode support structure assembly 12 can further comprise a third element 44. The third element 44 can comprise a generally cylindrical member having an outer radial surface 46 including a plurality of channels 48. Each of the plurality of channels 48 can be configured to receive the proximal end portion 26 of each of the plurality of splines 24. The channels 48 can extend along the axis (A) of the electrode support structure 22. The channels 48 can be configured to allow each of the plurality of splines 24 to move (e.g., slide) along the axis (A) of the electrode support structure 22. Accordingly, the third element 44 is configured to provide freedom for the splines 24 to move independently along the axis (A) of the electrode support structure 22. For example and without limitation, the third element 44 may be configured to allow each of the plurality of splines 24 to independently, axially travel a distance from 0 to about 0.100 inches (about 2.54 mm). Although this particular range for the distance is mentioned in detail, the third element 42 may be configured to allow each of the plurality of splines 24 to independently, axially travel a distance that is greater or smaller in accordance with other embodiments of the disclosure.

The proximal end portion 26 of each of the plurality of splines 24 can comprise a section configured to restrain the axial slide movement of each of the plurality of splines 24 so as to keep each of the plurality of splines 24 within the third element 42 of the electrode support structure assembly 12. For example and without limitation, the section of the proximal end portion 26 can comprise a shoulder 50. In other words, a proximal end 52 of the proximal end portion 26 of each of the plurality of splines 24 has an increased diameter relative to the remainder of the proximal end portion 26 of each of the plurality of splines 24, thereby forming the shoulder 50 in each of the plurality of splines 24.

Referring now to FIGS. 4-9, an electrode support structure assembly 112 in accordance with a second embodiment of the disclosure is generally illustrated. The electrode support structure assembly 112 can be similarly mounted to the distal end of the elongated catheter body 20 (see FIG. 1) and can be substantially identical to electrode support structure assembly 12 described above except for differences in the proximal end portion of each of the plurality of splines and differences in the elements configured to join the distal end portions of the splines as described hereinbelow. The electrode support structure assembly 112 can further comprise one or more electrodes (such as electrodes 54 shown in FIG. 2) supported by one or more of the plurality of splines 124. For example, one or more of the plurality of splines 124 can have one or more electrodes (such as electrodes 54 shown in FIG. 2) mounted on the non-conductive covering of each of the plurality of splines 124 in accordance with various embodiments of the disclosure. The number and spacing of the electrodes (such as electrodes 54 shown in FIG. 2) on the plurality of splines 124 can vary in accordance with various embodiments of the disclosure.

Figure 5:
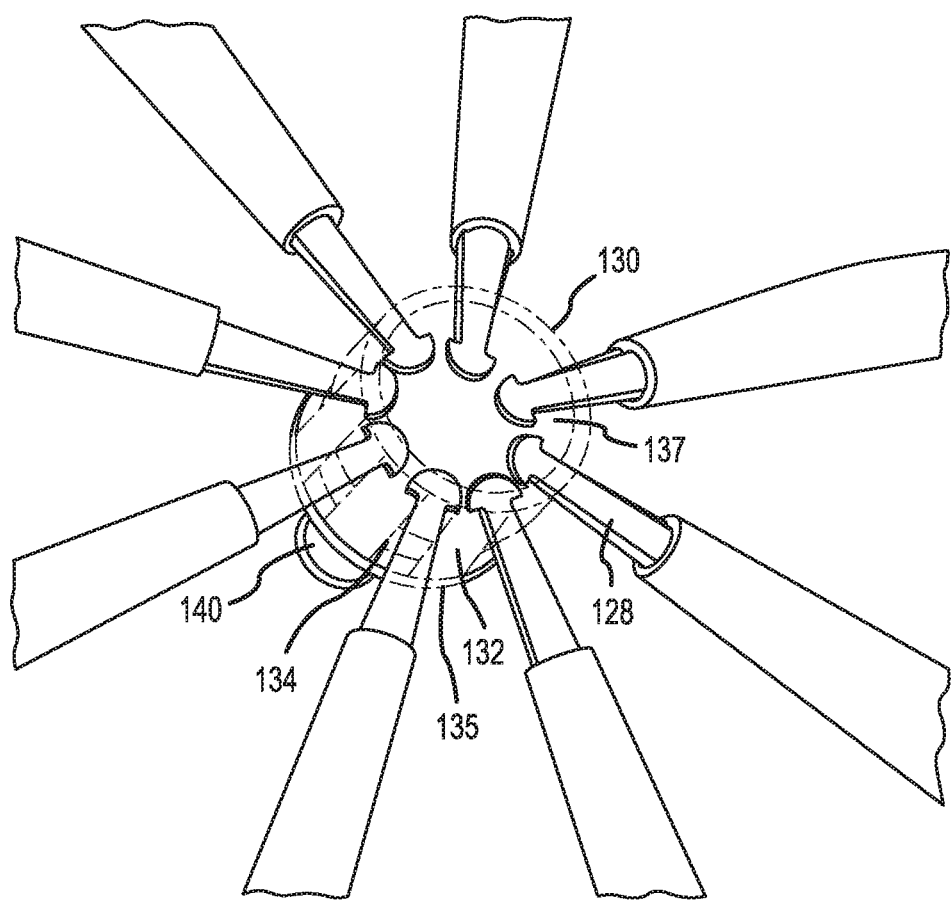
FIG. 5 is a distal isometric view of the electrode support structure assembly of FIG. 4.
Figure 6:
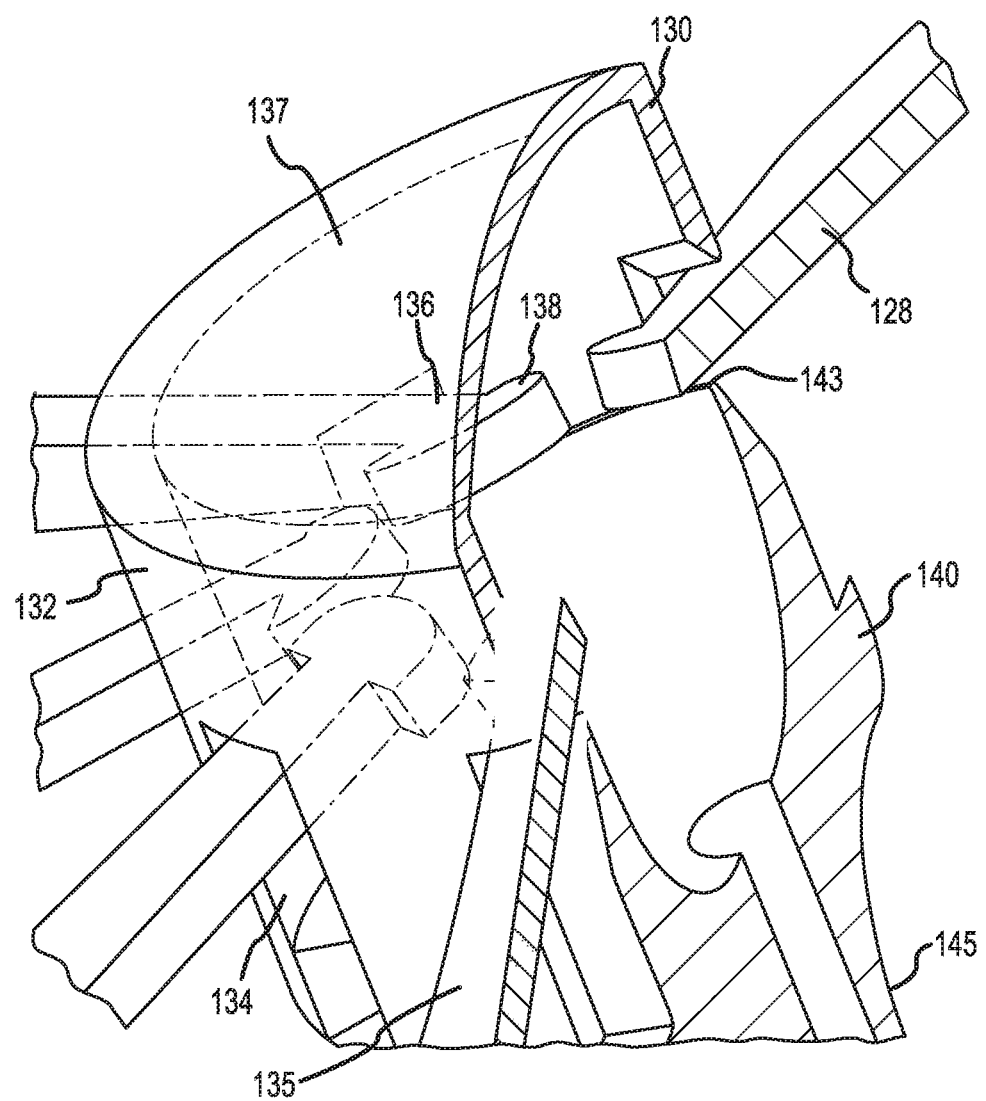
FIG. 6 is an isometric, cross-sectional view of the distal end of the electrode support structure assembly of FIG. 4.
Figure 7:
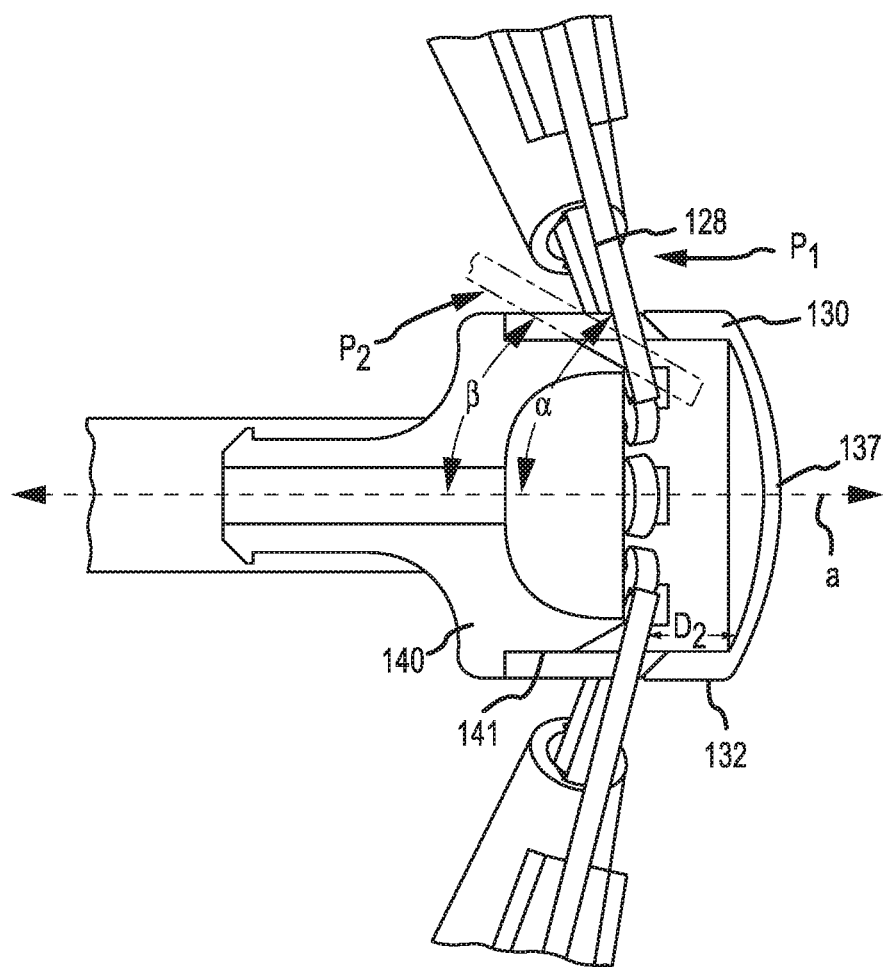
FIG. 7 is a cross-sectional view of the distal end of the electrode support structure assembly of FIG. 4.

The electrode support structure assembly 112 comprises a first element 130. Referring now to FIGS. 5-7 in particular, the first element 130 may be a cap having an axis (a) about which an outer radial surface 132 extends. The outer radial surface 132 of the first element 130 includes a plurality of slots 134. The outer radial surface 132 may be part of a radially extending wall 135. The cap 130 can further include an axial end 137. The axial end 137 can be separated from the second element 140 by a select distance $D_2$ (see FIG. 7) to allow for movement (e.g., distal articulation) of each of the plurality of splines 124. The plurality of slots 134 are substantially evenly circumferentially spaced around the outer radial surface 132 of the first element 130. Each of the plurality of slots 134 is configured to receive the distal end portion 128 of each of the plurality of splines 124. In accordance with an embodiment of the disclosure, each of the plurality of slots 134 can extend through the radially extending wall 135. Each of the plurality of slots 134 can extend parallel to or along the axis (a) of the first element 130.

Referring now to FIG. 7, each of the plurality of slots 134 is configured to allow each of the plurality of splines 124 to articulate from a first position $P_1$ in which the distal end portion 128 of the spline 124 is disposed at a first angle α relative to the axis (a) of the first element 130 to a second position $P_2$ (shown in dotted lines) in which the distal end portion 128 of the spline 124 is disposed at a second angle β relative to the axis (a) of the first element 130. The first angle α is different than the second angle β in accordance with various embodiments of the disclosure. For example and without limitation, position $P_1$ corresponds to the electrode support structure 122 in an expanded arrangement and position $P_2$ corresponds to the electrode support structure 122 in a collapsed arrangement. Under such circumstances, the first angle α is greater than the second angle β. The slots 134 are configured to allow each of the plurality of splines 124 to articulate relative to the axis (a) of the first element 130 Accordingly, the first element 130 is configured to provide freedom for the splines 124 to distally articulate relative to the axis (a) of the first element 130, thereby allowing for increased distal flexibility of the electrode support structure 122, improved collapsibility of the electrode support structure 122, and decreased axial and radial resistive force which might otherwise result in failure at the distal end of the electrode support structure assembly 112.

The distal end portion 128 of each of the plurality of splines 124 can comprise a section configured to retain each of the plurality of splines 124 within the first element 130 of the electrode support structure 112. For example and without limitation, the section of the distal end portion 128 can comprise a shoulder 136. In other words, a distal end 138 of the distal end portion 128 of each of the plurality of splines 124 has an increased diameter relative to the remainder of the distal end portion 128 of each of the plurality of splines 124, thereby forming the shoulder 136 in each of the plurality of splines 124.

Referring now to FIGS. 4-7, the electrode support structure assembly 112 comprises a second element 140 configured for engagement with the first element 130 to retain the distal end portion 128 of the each of the plurality of splines 124 within the plurality of slots 134 of the first element 130. In accordance with the second embodiment of the disclosure as generally illustrated in FIGS. 4-7, the second element 140 comprises a generally cylindrical member 140 with an outer radial surface 141 having at least a portion thereof configured to be disposed radially inwardly of the first element 130. The second element 140 can comprise a fluid coupler having a first end portion 143 (see FIG. 6) configured to mate with the first element 130 and a second end portion 145 (see FIG. 6) configured to mate with a tubing assembly (not shown). The tubing assembly may be connected to an irrigation system and include, for example and without limitation, an irrigation pump and can be configured to supply irrigation fluid to the fluid coupler, the fluid coupler configured to transfer the fluid to the electrode support structure assembly 112 at the distal end of the assembly. The fluid coupler 140 can also be configured to radially confine the plurality of splines 124.

Figure 4:
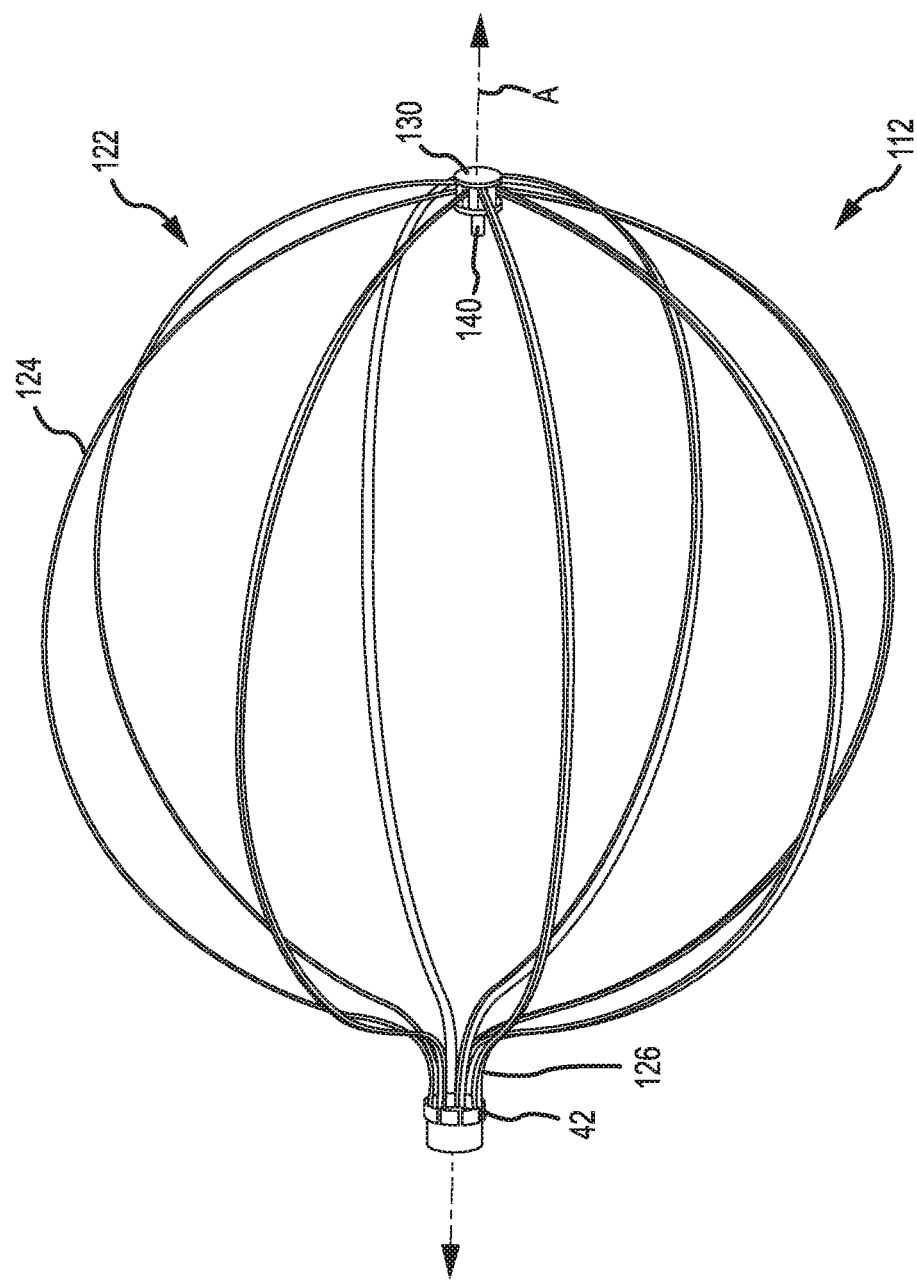
FIG. 4 is a perspective view of an electrode support structure assembly in accordance with a second embodiment of the disclosure.
Figure 8:
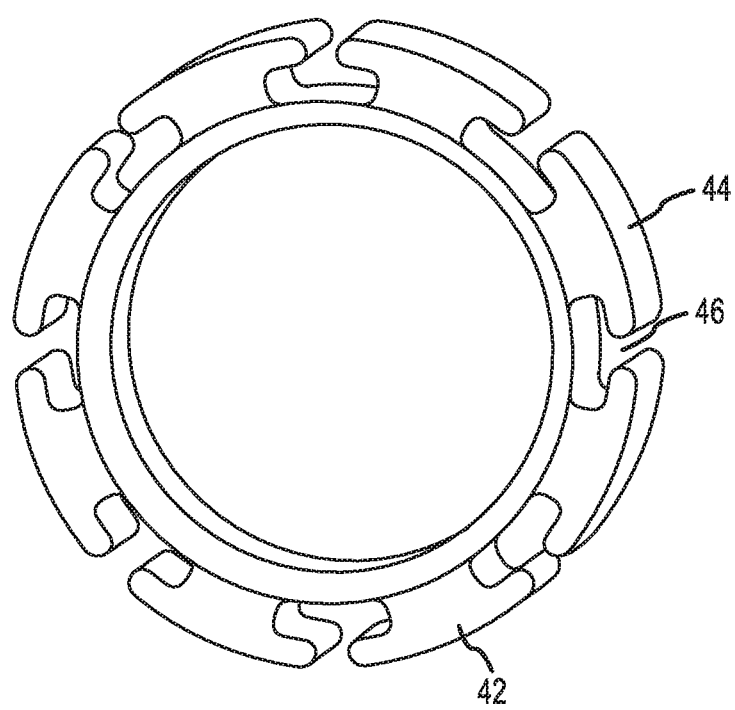
FIG. 8 is a perspective view of a proximal element of the electrode support structure assembly of FIG. 4.
Figure 9:
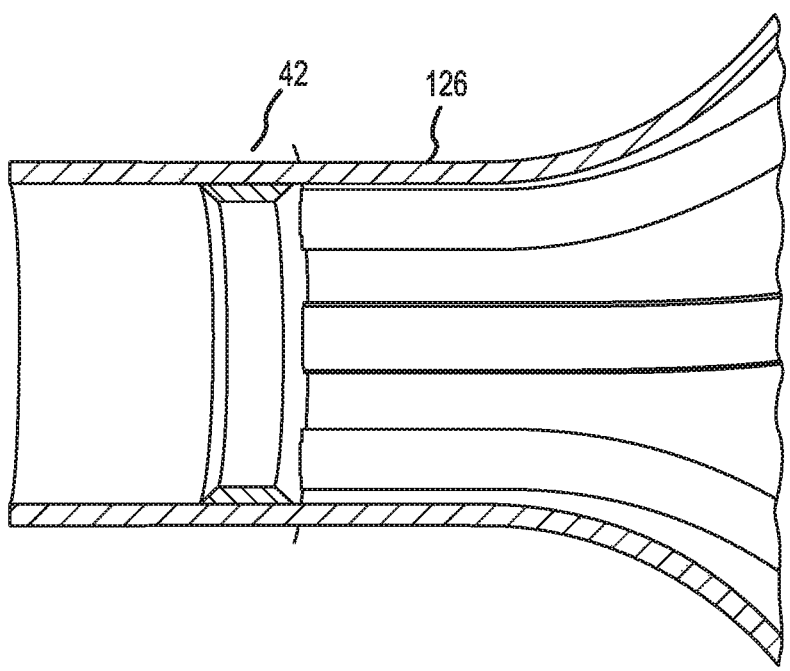
FIG. 9 is a cross-sectional view of the proximal end of the electrode support structure assembly of FIG. 4.

Referring now to FIGS. 4 and 8-9, in accordance with some embodiments of the disclosure, the electrode support structure assembly 112 can further comprise a third element 42. The third element 42 can comprise a generally cylindrical member having an outer radial surface 44 including a plurality of channels 46. Each of the plurality of channels 46 can be configured to receive the proximal end portion 126 of each of the plurality of splines 124. The channels 146 can extend parallel to or along the axis (A) of the electrode support structure 122. Referring now to FIG. 9, in accordance with an embodiment of the disclosure, the proximal end portion 126 of each of the plurality of splines 124 can be formed by laser cutting a tube, such that the proximal end portion 126 of each of the plurality of splines 124 are integral. Although the proximal end portion 126 of each of the plurality of splines 124 are described and illustrated as being formed by laser cutting a tube, such as a metallic Nitinol tube, the proximal end portions 126 of each of the plurality of splines 124 may be independently moveable at a proximal end as described and illustrated in connection with the first embodiment of the disclosure.

Figure 10:
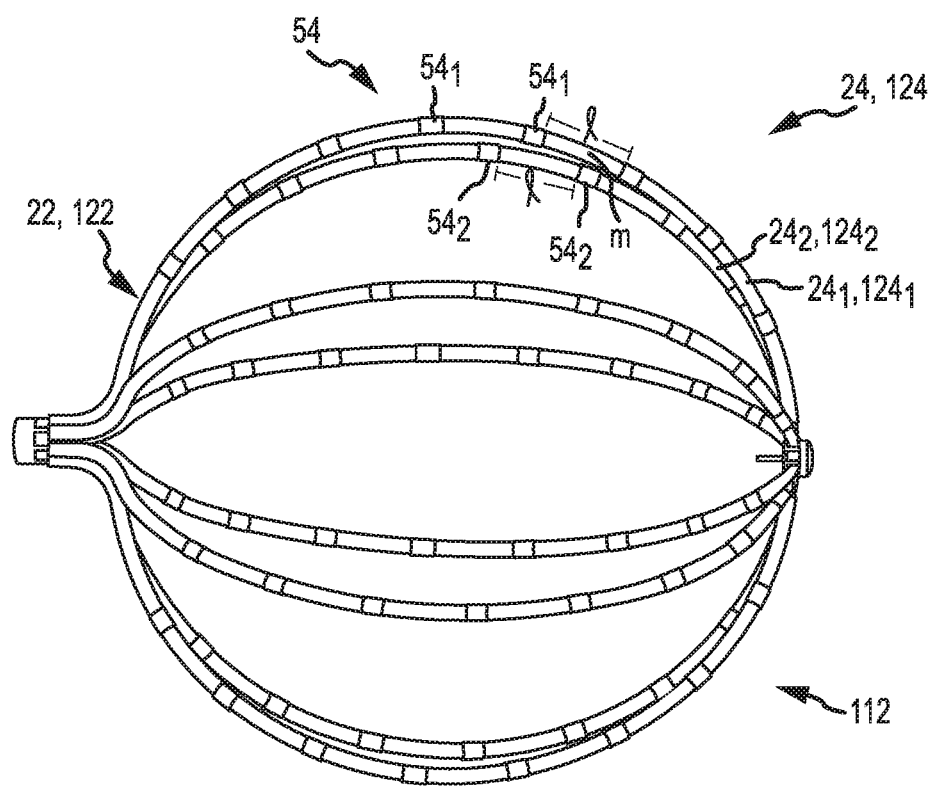
FIG. 10 is a lateral elevational view of an electrode support structure having an improved electrode arrangement in accordance with a third embodiment of the disclosure.
Figure 11:
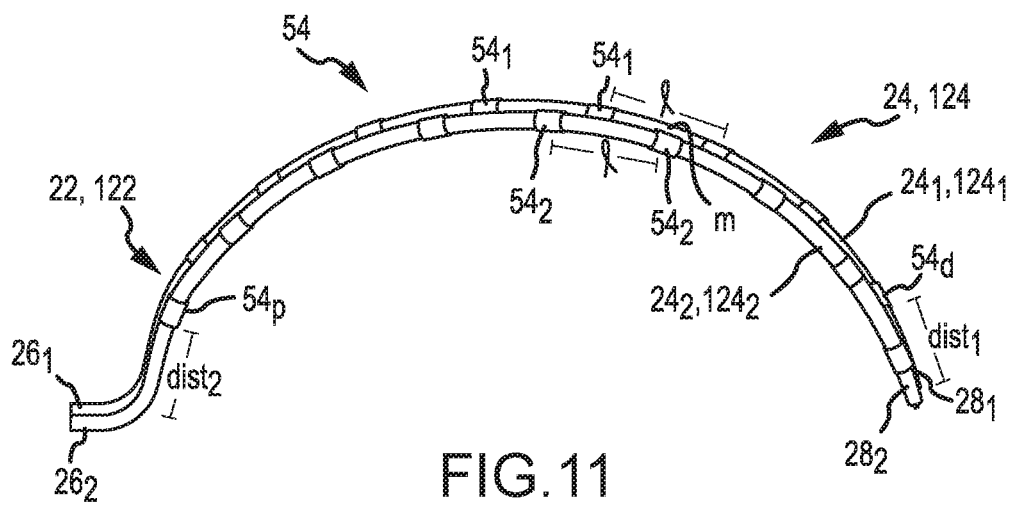
FIG. 11 is a lateral elevational view of a portion of the electrode support structure of FIG. 10.

Referring now to FIGS. 10-11, each of the plurality of splines 24, 124 can have one or more electrodes 54 mounted on the non-conductive covering in accordance with some embodiments of the disclosure. Reference herein to splines 24 includes one or more of splines $24_1$ and/or $24_2$. Reference herein to splines 124 includes one or more of $124_1$ and/or $124_2$. The electrodes 54 mounted on each of the plurality of splines 24, 124 can comprise ring electrodes in accordance with an embodiment of the disclosure. Each of the electrodes 54 on the splines 24, 124 is electrically connected to the visualization, navigation, and/or mapping system (not shown) such as those systems available under the name ENSITE NAVX™ (aka ENSITE™ Classic as well as newer versions of the ENSITE™ system, denoted as ENSITE VELOCITY™) and available from St. Jude Medical, Inc. (not shown) and/or a source of ablation energy by means of an electrode lead wire (not shown). Each electrode lead wire extends through the control handle 14, through a lumen in the elongated catheter body 20, and into the non-conductive covering of a corresponding spline 24, 124. Each lead wire is attached to its corresponding electrode 54 by any suitable method known to those of ordinary skill in the art. An exemplary method for attaching a lead wire to an electrode 54 involves making a small hole through the wall of the non-conductive covering. For example and without limitation, a needle may be inserted through the non-conductive covering and heated sufficiently to form a permanent hole. The lead wire can then be drawn through the hole by using a microhook or similar structure. The lead wire can then be stripped of any coating and welded to the underside of the electrode 54, which can then be slid into position over the hole and fixed in place with polyurethane glue or the like. Alternatively, each electrode 54 can be formed by wrapping a lead wire around the non-conductive covering a number of times and stripping the lead wire of its own insulated coating on radially outwardly extending surfaces.

One or more of the splines 24, 124 can include at least one electrode 54. Reference herein to electrode 54 includes one or more of electrodes $54_1$ and/or $54_2$. In various embodiments, each spline 24, 124 can include multiple electrodes 54 spaced along substantially the entire length of the spline 24, 124. The electrodes 54 along a spline 24, 124 or along each of the plurality of splines 2, 124 may be the same or different in size. In accordance with a third embodiment of the disclosure, the electrode support structure assembly 12, 112 comprises an electrode support structure 22, 122 including an even number of splines 24, 124. Each of the plurality of splines 24, 124 can include an equal number of electrodes 54 disposed thereon. Each of the electrodes 54 can be substantially evenly spaced along the length of each of the plurality of splines 24, 124. In accordance with the third embodiment of the disclosure, the plurality of splines 24, 124 includes at least a first spline $24_1$, $124_1$ and a second spline $24_2$, $124_2$. The first spline $24_1$, $124_1$ includes a first plurality of electrodes $54_1$ substantially evenly spaced apart on the first spline. The distance between adjacent electrodes $54_1$ on the first spline $24_1$, $124_1$ may be a selected length (l). The second spline $24_2$, $124_2$ includes a second plurality of electrodes $54_2$ substantially evenly spaced apart on the second spline. The distance between adjacent electrodes $54_2$ on the second spline $24_2$, $124_2$ may be a selected length (l) substantially equal to the selected length (l) between adjacent electrodes $54_1$ on the first spline $24_1$, $124_1$. Each of the second plurality of electrodes $54_2$ on the second spline $24_2$, $124_2$ is in a staggered position relative to the position of each of the first plurality of electrodes $54_1$ on the first spline $24_1$, $124_1$. In particular, at least one of the second plurality of electrodes $54_2$ on the second spline $24_2$, $124_2$ is located on the second spline $24_2$, $124_2$ at a position that is substantially in a plane that is transverse to a longitudinal axis of the second spline $24_2$, $124_2$ and containing the midpoint (m) between two of the first plurality of electrodes $54_1$ on the first spline $24_1$, $124_1$. Accordingly, the electrodes $54_1$, $54_2$ are positioned alternately such that the electrodes $54_1$, $54_2$ on adjacent splines $24_1$, $124_1$, $24_2$, $124_2$ do not coincide with each other, but fall within the middle of the space of length (l) between electrodes $54_1$, $54_2$ on the adjacent spline $24_1$, $124_1$, $24_2$, $124_2$.

An electrode arrangement in accordance with the third embodiment of the disclosure may provide for more uniform electrode distribution about a surface of the spheroid formed by the electrode support structure 22, 122, thereby potentially resulting in improved mapping. An electrode arrangement in accordance with the third embodiment of the disclosure may also be configured to prevent electrode to electrode short circuits when the electrode support structure 22, 122 is in its collapsed or partially collapsed state (e.g., when emerging from or being pulled in to a delivery sheath). An electrode arrangement in accordance with the third embodiment of the disclosure may also allow a smaller profile when the electrode support structure 22, 122 is being delivered through a tortuously angulated pathway.

In accordance with the third embodiment of the disclosure, each spline $24_1$, $124_1$, may be symmetric with each adjacent spline $24_2$, $124_2$ In other words, each spline $24_1$, $124_1$, $24_2$, $124_2$ can have the same electrode layout when flipped proximal end to distal end. In accordance with such an arrangement, a first distance $dist_1$ between a distal-most electrode $54_d$ of the first plurality of electrodes $54_1$ and a distal end $28_1$ of the first spline $24_1$, $124_1$ is substantially the same as a second distance $dist_2$ between a proximal-most electrode $54_p$ of the second plurality of electrodes $54_2$ and a proximal end $26_2$ of the second spline $24_2$, $124_2$ Although these particular electrode arrangements are mentioned and illustrated in detail, there may be additional electrode arrangements that be utilized in accordance with various embodiments of the disclosure. For example and without limitation, spacing between electrodes 54 can vary based on the length of splines $24_1$, $124_1$, $24_2$, $124_2$ or the desired distance from the proximal and distal ends 26, 28 of the splines $24_1$, $124_1$, $24_2$, $124_2$.

Figure 12A:
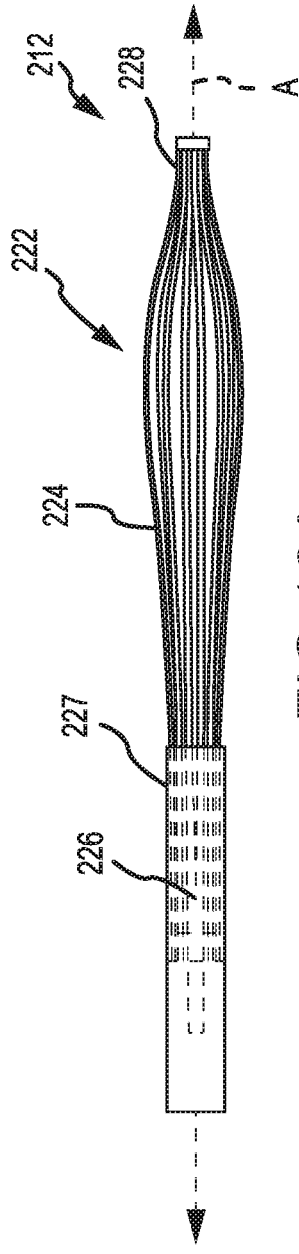
Figure 12B:
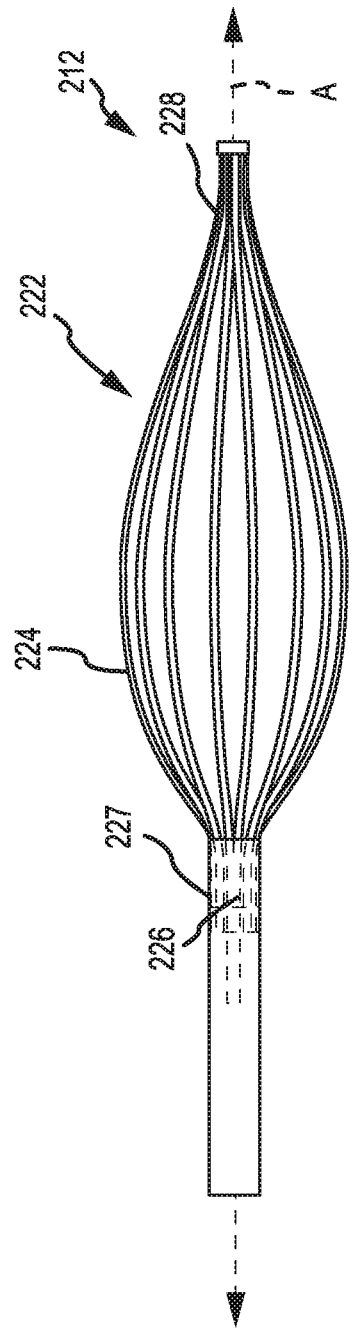

In accordance with a fourth embodiment of the disclosure and with reference to FIGS. 12A-12C, an electrode support structure assembly 212 including an electrode support structure 222 and a sheath 227 is generally illustrated. The electrode support structure assembly 212 in accordance with the fourth embodiment of the disclosure can be configured to better provide for diametric collapse disproportionate to axial retraction, which may allow for free, uniform axial displacement even when the electrode support structure assembly 212 is being diametrically constrained in some way. Each of the plurality of splines 224 forming the electrode support structure 222 can comprise a Nitinol wire with a non-conductive covering (not shown), such as polyurethane or polyimide tubing, and electrodes (not shown) interspersed along the splines 224, as described above. Although these materials are mentioned in detail, the splines 224 can be made of any other suitable materials known to those of ordinary skill in the art. Each of the plurality of splines 224 has a proximal end portion 226 and a distal end portion 228 opposing the proximal end portion 226. For example and without limitation, the electrode support structure 222 may include eight splines 224. Although eight splines 224 are mentioned in detail, there may be fewer or more splines 224 in accordance with various embodiments of the disclosure. Each of the plurality of splines 224 may generally be evenly spaced circumferentially around a longitudinal axis (A) defined by the electrode support structure 222. The electrode support structure 222 is configured to be radially outwardly expandable relative to its axis (A) to an expanded arrangement as shown in FIG. 12C. The electrode support structure 222 is also configured to be radially inwardly collapsible relative to its axis (A) to a collapsed arrangement as shown in FIG. 12A. The expansion and collapse of the electrode support structure 222 may be achieved using a shape memory material having a preset shape for the plurality of splines 224 in accordance with the fourth embodiment of the disclosure. Accordingly, no separate mechanical biasing mechanism, such as an expander or tensor, may be needed in accordance with the fourth embodiment of the disclosure. The use of an expander or tensor may impinge upon free axial movement of the electrode support structure 222 when the electrode support structure 222 is diametrically impinged upon from a distal-most direction, for example.

Referring now to FIG. 12A, the proximal end portion 226 of each of the plurality of splines 224 of the electrode support structure 222 is contained and constrained within a recess of an outer sheath 227. The electrode support structure 222 is in its collapsed arrangement. Referring now to FIG. 12B, the proximal end portion 226 of each of the plurality of splines 224 of the electrode support structure 222 are partially advanced from the recess within the outer sheath 227, thereby allowing the electrode support structure 222 to partially return to its preset shape. For example and without limitation, the proximal end portion 226 of each of the plurality of splines 224 of the electrode support structure 222 may be advanced out of the outer sheath 227 about 0.125 inches (about 3.175 mm). Although this particular distance is mentioned in detail, the proximal end portion 226 of each of the plurality of splines 224 of the electrode support structure 222 may be advanced out of the outer sheath 227 a greater or lesser amount in accordance with various embodiments of the disclosure. The electrode support structure 222 may appear more spherical as it advanced out of the outer sheath 227. Movement of the proximal end portion 226 of each of the plurality of splines 224 of the electrode support structure 222 relative to the sheath 227 is configured to expand and collapse the electrode support structure 222.

Referring now to FIG. 12C, the proximal end portion 226 of each of the plurality of splines 224 of the electrode support structure 222 are fully advanced from the recess within the outer sheath 227, thereby allowing the electrode support structure 222 to fully return to its preset shape. For example and without limitation, the proximal end portion 226 of each of the plurality of splines 224 of the electrode support structure 222 may be advanced out of the outer sheath 227 about 0.25 inches (about 6.35 mm). Although this particular distance is mentioned in detail, the proximal end portion 226 of each of the plurality of splines 224 of the electrode support structure 222 may be advanced out of the outer sheath 227 a greater or lesser amount in accordance with various embodiments of the disclosure. The electrode support structure 222 may appear substantially spherical as it is fully advanced out of the outer sheath 227.

Figure 13:
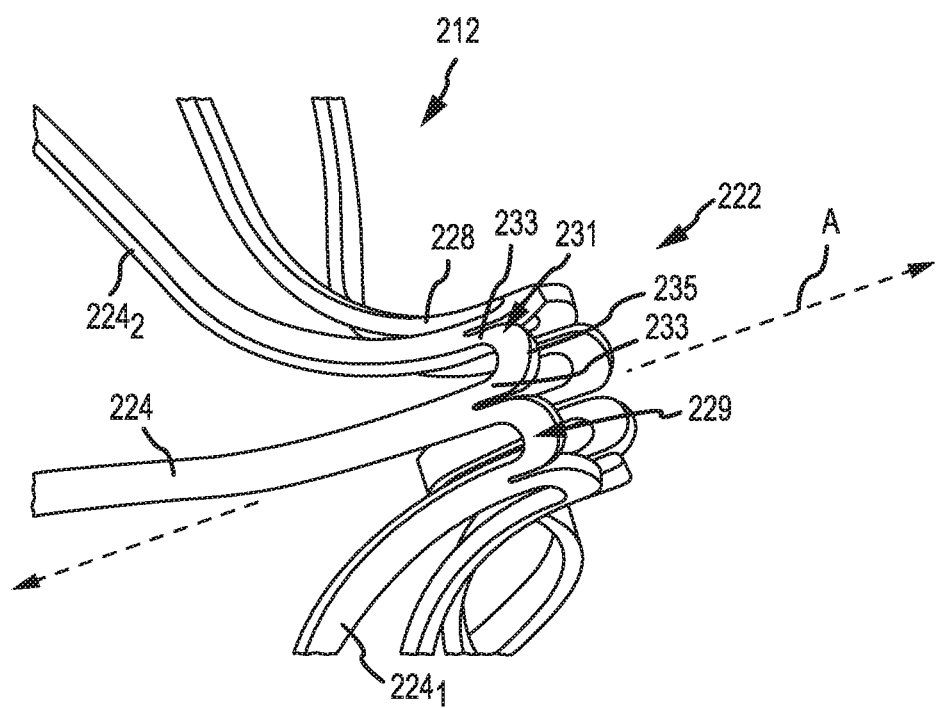
FIG. 13 is a close-up view of a distal end of the electrode support structure of FIGS. 12A-12C.

Referring now to FIG. 13, a close up view of the distal end portion 228 of each of the plurality of splines 224 of the electrode support structure 222 is generally illustrated. The distal end portion 228 of each of the plurality of splines 224 of the electrode support structure 222 comprises a first connection element 229 configured to connect the distal end portion 228 of one of the plurality of splines 224 to a first adjacent spline 224₁. The distal end portion 228 of each of the plurality of splines 224 of the electrode support structure 222 further comprises a second connection element 231 configured to connect the distal end portion 228 of one of the plurality of splines 224 to a second adjacent spline 224₂. The first connection element 229 and second connection element 231 can each comprise a U-shaped member having two substantially parallel legs 233 joined by a curved base 235. Each of the legs 233 are disposed substantially parallel to the axis (A) of the electrode support structure 222. While the connection elements 229, 231 are described as U-shaped having two substantially parallel legs 233 joined by a curved base 235, the connection elements 229, 231 can take any number of various other shapes in accordance with various embodiments of the disclosure. The first connection element 229, second connection element 231, and each of the plurality of splines 224 are integrally formed in accordance with the fourth embodiment of the disclosure. Accordingly, the first connection element 229, second connection element 231, and each of the plurality of splines 224 are formed as a single, one-piece, unitary, monolithic structure. At least a portion of the distal end portion 228 of each of the plurality of splines 224 are disposed substantially along the axis (A) of the electrode support structure 222.

Although at least four embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An electrode support structure assembly comprising:
   an electrode support structure comprising a plurality of splines, wherein each of the plurality of splines extends from a proximal end to a distal end;
   a first element defining an axis and comprising an outer section, wherein the outer section comprises a plurality of slots configured to receive a connection portion of each of the plurality of splines;
   a second element comprising a fluid coupler, wherein the second element is configured to engage with the first element, and wherein the fluid coupler is configured to couple to a fluid lumen,
   wherein the fluid coupler is configured to deliver a fluid to an internal portion of the first element and the second element.

2. The electrode support structure assembly of claim 1, wherein each of the plurality of splines comprises a section configured for engagement with the first element.

3. The electrode support structure assembly of claim 1, wherein each of the plurality of splines comprises a first connection element, and wherein the first connection element is configured to couple to a first adjacent spline.

4. The electrode support structure assembly of claim 3, wherein the first connection element comprises a U-shaped member.

5. The electrode support structure assembly of claim 4, wherein the U-shaped member comprises two parallel legs and a curved base.

6. The electrode support structure assembly of claim 3, wherein each of the plurality of splines further comprises a second connection element, and wherein the second connection element is configured to couple to a second adjacent spline.

7. The electrode support structure assembly of claim 6, wherein the first connection element comprises a first U-shaped member and the second connection element comprises a second U-shaped member.

8. The electrode support structure assembly of claim 1, further comprising a tubing assembly coupled to the fluid coupler, wherein the tubing assembly is configured to deliver a fluid to the fluid coupler.

9. The electrode support structure assembly of claim 1, wherein the plurality of slots are configured to deliver the fluid from an internal portion of the first element and the second element to a portion of the plurality of splines external the first element and the second element.

10. The electrode support structure assembly of claim 1, wherein the plurality of slots are configured to deliver the fluid towards a portion of the plurality of splines external the first element and the second element.

11. The electrode support structure assembly of claim 1, wherein the plurality of splines comprise nitinol.

12. The electrode support structure assembly of claim 1, wherein the connection portion of each of the plurality of splines comprises a first connection portion and further comprising a second element comprising a generally cylindrical member having an outer radial surface including a plurality of channels configured to receive a second connection portion of each of the plurality of splines.

13. The electrode support structure assembly of claim 1, wherein the first element comprises a cap having an axial end and a radially extending wall and wherein each of the plurality of slots extend through the radially extending wall.

14. The electrode support structure assembly of claim 13, wherein each of the plurality of slots extends along the axis of the first element and is configured to allow each of the plurality of splines to articulate from a first position in which a distal end portion of the spline is disposed at a first angle relative to the axis of the first element to a second position in which the distal end portion of the spline is disposed at a second angle relative to the axis of the first element and wherein the first angle is different than the second angle.

15. The electrode support structure assembly of claim 1, wherein the plurality of splines includes a first spline and a second spline, wherein the first spline includes a first plurality of electrodes spaced apart on the first spline, wherein the second spline includes a second plurality of electrodes spaced apart on the second spline, wherein each of the second plurality of electrodes on the second spline is in a staggered position relative to the position of each of the first plurality of electrodes on the first spline.

16. The electrode support structure assembly of claim 15, wherein at least one of the second plurality of electrodes on the second spline is located on the second spline at a position that is in substantially the same plane as the midpoint between two of the first plurality of electrodes on the first spline.

17. The electrode support structure assembly of claim 15, wherein a first distance between a distal-most electrode of the first plurality of electrodes and a distal end of the first spline is substantially the same as a second distance between a proximal-most electrode of the second plurality of electrodes and a proximal end of the second spline.

18. An electrode support structure assembly comprising:
an electrode support structure defining a longitudinal axis, wherein the electrode support structure is configured to be outwardly expandable relative to the longitudinal axis to an expanded arrangement and inwardly collapsible relative to the longitudinal axis to a collapsed arrangement, the electrode support structure comprising:
a plurality of splines, wherein a distal connection portion of at least one of the plurality of splines comprises a first connection element and a second connection element, wherein the first connection element and the second connection element are integrally formed with the at least one of the plurality of splines, and wherein the first connection element is configured to couple to a first adjacent spline and the second connection element is configured to couple to a second adjacent spline; and
a first element defining an axis and comprising an outer section, wherein the outer section comprises a plurality of slots configured to receive the connection portion of each of the plurality of splines.

19. The electrode support structure assembly of claim 18, wherein the first connection element comprises a first U-shaped member and the second connection element comprises a second U-shaped member.

20. The electrode support structure assembly of claim 19, wherein the first U-shaped member and the second U-shaped member each comprises two parallel legs and a curved base.

* * * * *